United States Patent
Shetty (10) Patent No.: US 10,646,525 B2
(45) Date of Patent: May 12, 2020

(54) HERBAL COMPOSITION FOR TREATMENT AND MANAGEMENT OF INFECTIOUS DISEASES AND METHOD OF PREPARATION THEREOF

(71) Applicant: Muniyal Ayurvedic Research Centre, Manipal (IN)

(72) Inventor: M Vijayabhanu Shetty, Manipal (IN)

(73) Assignee: Muniyal Ayurvedic Research Centre, Manipal (IN)

(*) Notice: Subject to any disclaimer, the term of this patent is extended or adjusted under 35 U.S.C. 154(b) by 0 days.

(21) Appl. No.: 16/233,896

(22) Filed: Dec. 27, 2018

(65) Prior Publication Data

US 2019/0134124 A1     May 9, 2019

Related U.S. Application Data

(60) Provisional application No. 62/612,971, filed on Jan. 2, 2018.

(51) Int. Cl.

| | | |
|---|---|---|
| *A61K 36/185* | (2006.01) | |
| *A61P 31/04* | (2006.01) | |
| *A61K 36/328* | (2006.01) | |
| *A61K 36/58* | (2006.01) | |
| *A61K 36/9066* | (2006.01) | |
| *A61K 33/04* | (2006.01) | |
| *A61K 33/26* | (2006.01) | |
| *A61K 33/34* | (2006.01) | |
| *A61K 33/22* | (2006.01) | |
| *A61K 35/618* | (2015.01) | |
| *A61K 45/06* | (2006.01) | |
| *A61K 36/67* | (2006.01) | |
| *A61K 36/24* | (2006.01) | |
| *A61K 36/882* | (2006.01) | |
| *A61K 36/9068* | (2006.01) | |
| *A61K 36/81* | (2006.01) | |
| *A61K 36/748* | (2006.01) | |
| *A61K 36/428* | (2006.01) | |
| *A61K 36/51* | (2006.01) | |
| *A61K 36/59* | (2006.01) | |
| *A61K 36/8905* | (2006.01) | |
| *A61K 36/68* | (2006.01) | |
| *A61K 36/9062* | (2006.01) | |
| *A61K 36/484* | (2006.01) | |
| *A61P 31/10* | (2006.01) | |

(52) U.S. Cl.
CPC ............ *A61K 36/185* (2013.01); *A61K 33/04* (2013.01); *A61K 33/22* (2013.01); *A61K 33/26* (2013.01); *A61K 33/34* (2013.01); *A61K 35/618* (2013.01); *A61K 36/24* (2013.01); *A61K 36/328* (2013.01); *A61K 36/428* (2013.01); *A61K 36/484* (2013.01); *A61K 36/51* (2013.01); *A61K 36/58* (2013.01); *A61K 36/59* (2013.01); *A61K 36/67* (2013.01); *A61K 36/68* (2013.01); *A61K 36/748* (2013.01); *A61K 36/81* (2013.01); *A61K 36/882* (2013.01); *A61K 36/8905* (2013.01); *A61K 36/9062* (2013.01); *A61K 36/9066* (2013.01); *A61K 36/9068* (2013.01); *A61K 45/06* (2013.01); *A61P 31/04* (2018.01); *A61P 31/10* (2018.01); *A61K 2236/15* (2013.01)

(58) Field of Classification Search
CPC .. A61K 2300/00; A61K 36/185; A61K 36/48; A61K 36/59; A61K 36/67; A61K 36/81; A61K 36/9066; A61K 36/24; A61K 36/328; A61K 33/26; A61K 36/264; A61K 36/28; A61K 36/61; A61K 36/68; A61K 36/714; A61K 36/748; A61K 36/77; A61K 36/882; A61K 36/8905; A61K 36/9062; A61K 36/9068; A61K 33/00; A61K 33/30; A61K 33/34; A61K 35/04; A61K 45/06; A61K 9/205; A61K 2236/15; A61K 33/04; A61K 33/22; A61K 33/28; A61K 35/614; A61K 35/618; A61K 36/428; A61K 36/484; A61K 36/51; A61K 36/58; A61K 9/20; A61P 31/04; A61P 31/10; A61P 35/00; A61P 5/14

See application file for complete search history.

(56) References Cited

PUBLICATIONS

Pal D, et al "Bhasma: The Ancient Indian Nanomedicine" Journal of Advanced Pharmaceutical Technology & Research | Jan.-Mar. 2014 (pub Feb. 13, 2014), 5(1), pp. 4-12; doi: 10.4103/2231-4040. 126980 (Year: 2014).*

Bhowmick, T.K., Suresh, A.K., Kane, S.G., et al "Physicochemical characterization of an Indian traditional medicine, Jasada Bhasma: detection of nanoparticles containing non-stoichiometric zinc oxide" J Nanopart Res, 2009 (online pub Jul. 3, 2008),11(3), pp. 655-664; doi 10.1007/s11051-008-9414-z (Year: 2008).*

* cited by examiner

*Primary Examiner* — Aaron J Kosar (74) *Attorney, Agent, or Firm* — Pilloff Passino & Cosenza LLP; Sean A. Passino; Rachel K. Pilloff (57) ABSTRACT

Herbal composition for treatment and management of Infectious diseases and method of preparation are disclosed herein. The disclosed composition including herbs and bhasmas may be used to treat Infectious diseases such as bacterial infection, fungal infection, viral infections, Pharyngitis, Laryngitis and Bronchitis etc. The method disclosed herein may be used as the main line of treatment or as supportive medication.

22 Claims, 5 Drawing Sheets

HERBAL COMPOSITION FOR TREATMENT AND MANAGEMENT OF INFECTIOUS DISEASES AND METHOD OF PREPARATION THEREOF

CROSS REFERENCE TO RELATED APPLICATION

This application is based on and derives the benefit of U.S. Provisional Application 62/612,971 filed on the 2 Jan. 2018, the contents of which are incorporated herein by reference in their entirety.

TECHNICAL FIELD

The embodiments disclosed in this specification relates to herbal composition effective in treatment and management of Infectious diseases. It also relates to the process for preparation of such composition.

BACKGROUND

Infection is the invasion of an organism's tissue by micro-organisms. Further growth and multiplication of these micro-organisms within the tissue leads to disorders of the infected tissues. In humans, infections of organ tissue such as ear, skin, stomach, throat, etc. are common. These infections are transmittable and may easily spread under lack of proper care and hygiene. These infectious micro-organisms include bacteria, virus, protozoa among others.

Antibiotics are a common line of treatment used against bacterial infections. They kill or inhibit the growth of bacteria. However, in recent times, the overuse of antibiotics has resulted in an increase in drug resistant bacteria. While there is an increase in the bacterial strains that are resistant to conventional antibiotics, the development of new antibiotics is dwindling.

Alternatively, Ayurveda appears to be promising in combating such infectious diseases. Naturally existing herbs and medicaments made out of such herbs include numerous active compounds, which, unlike antibiotics, collectively work towards disarming the microbes. Herbs such as *Aloe*, turmeric, Ginger, Garlic, Acacia, Licorice and *Eucalyptus* are well known for their antibacterial properties. However, there exists a need for an effective method of treating/ managing Infectious diseases.

OBJECT OF THE DISCLOSED EMBODIMENTS

The principal object of the embodiments disclosed herein is to provide a method of treating Infectious diseases.

A second object of the embodiments disclosed herein is to provide a method of management of Infectious diseases.

Another object of the embodiments disclosed herein is to provide herbal composition and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings. The embodiments herein will be better understood from the following description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those skilled in the art to practice the embodiments herein. Accordingly, the examples should not be construed as limiting the scope of the embodiments herein.

The embodiments herein achieve an herbal composition of therapeutic value, and a process for the preparation of the same. The herbal composition disclosed herein is useful in the treatment and management of Infectious diseases. The composition disclosed in the various embodiments herein, may be used to treat infections of micro-organisms such as gram negative bacteria, gram positive bacteria, fungus, etc. Further, in various embodiments, the disclosed composition may also be used to treat wounds and ulcers. The various infectious diseases that may be treated by the disclosed composition include disorders of the skin, respiratory system such as bronchitis, pharyngitis, laryngitis, etc. Accordingly, the embodiments disclosed herein achieve a method for the treatment/management of Infectious diseases. The Disclosed composition, in various embodiments, may be used as a main line of treatment or as supportive medication in addition to other line of medication including allopathy, homeopathy, unani, naturopathy among others Composition The disclosed embodiments herein provide an herbal composition having combination of selected herbs and minerals. In an embodiment, the herbal composition includes herbs and minerals. In another embodiment, the herbal composition includes herbs, minerals and a suitable excipient.

Herb

In an embodiment, the composition includes the herbs *Emblica officinalis, Terminalia chebula, Terminalia bellerica, Commiphora mukul, Azadirachta indica* and *Curcuma longa*; or their extracts; or the active ingredients extracted from these herbs.

In another embodiment, the composition further includes the herbs *Piper longum, Solanum xanthocarpum, Tinospora cordifolia, Trichosanthes dioica, Holarrhena antidysenterica, Cyperus rotundus, Swertia chirata, Picrorhiza kur-* roa, *Zingiber officinale*, *Piper nigrum*, *Alpinia galanga*, *Glycyrrhiza glabra*, *Acorus calamus* and *Oldenlandia corymbosa*; or their extracts; or the active ingredients extracted from these herbs.

In an embodiment, the composition may include specific parts of the herb (also referred as herb component) such as roots, fruits, bark, stem, leaves, rhizome, etc. In an embodiment, the herb element includes fruits of *Emblica officinalis*, *Piper longum*, *Piper nigrum*, *Terminalia chebula* and *Terminalia bellerica*; oleo gum resin of *Commiphora mukul*; stem bark of *Azadirachta indica* and *Holarrhena antidysenterica*; rhizome of *Curcuma longa*, *Acorus calamus* and *Zingiber officinale*; whole plant of *Solanum xanthocarpum*, *Oldenlandia corymbosa*, *Trichosanthes dioica* and *Swertia chirata*; stem of *Tinospora cordifolia*; tuber of *Cyperus rotundus*; roots of *Picrorhiza kurroa*, *Alpinia galanga* and *Glycyrrhiza glabra*; or their extract. However, it is also within the scope of the claims provided herein for the herbal composition to include other herb components such as leaf, flowers, etc. without otherwise deterring intended function of the poly herbal composition.

In an embodiment, the composition includes *Emblica officinalis* in an amount in the range of 6 to 10 wt %, *Terminalia chebula* in an amount in the range of 6 to 10 wt %, *Terminalia bellerica* in an amount in the range of 6 to 10 wt %, *Commiphora mukul* in an amount in the range of 6 to 10 wt %, *Azadirachta indica* in an amount in the range of 6 to 10 wt %, and *Curcuma longa* in an amount in the range of 6 to 10 wt %, of the total weight of the composition.

In another embodiment, the composition further includes *Piper longum* in an amount of ≤2 wt %, *Solanum xanthocarpum* in an amount of ≤2 wt %, *Tinospora cordifolia* in an amount of ≤2 wt %, *Trichosanthes dioica* in an amount of ≤2 wt %, *Holarrhena antidysenterica* in an amount of ≤2 wt %, *Cyperus rotundus* in an amount of ≤2 wt %, *Swertia chirata* in an amount of ≤2 wt %, *Picrorhiza kurroa* in an amount of ≤2 wt %, *Zingiber officinale* in an amount of ≤2 wt %, *Piper nigrum* in an amount of ≤2 wt %, *Alpinia galanga* in an amount of ≤2 wt %, *Glycyrrhiza glabra* in an amount of ≤2 wt %, *Acorus calamus* in an amount of ≤2 wt %, and *Oldenlandia corymbosa* in an amount of ≤2 wt %, of the total weight of the composition.

The herb component of the herbs, disclosed herein, maybe included in the composition in any form that is generally known in the field. For example, the herb component may be processed to form extracts, dried, powdered, pelleted, concentrated, etc. In an embodiment, the herb components are dried and powdered which is further incorporated into the composition.

Minerals

In an embodiment, the composition includes minerals in the form of Bhasmas or calcined preparations such as Tankana Bhasma, Swarna makshika Bhasma, Muktha Sukthi Bhasma and Kapardika bhasma. Alternatively, the composition may also include at least one mineral selected from a group consisting of borax, pearl oyester, haematite, cowries and copper pyrite. In the disclosed embodiments, the bhasmas along with the herbs form bioavailable herbal complexes which are useful in treating Infectious diseases. In another embodiment, the composition includes pure minerals such as Sulphur (also referred to as Gandhaka). In an embodiment, the composition includes Shuddha gairika or haematite. However, it is also within the scope of claims provided herewith for the herbal composition to include, as a substitute or additionally, other similar calcined preparations or minerals without otherwise deterring from the intended function of the herbal composition.

In an embodiment, the composition includes Tankana Bhasma in an amount of ≤2 wt %, Swarna makshika Bhasma in an amount of ≤2 wt %, Muktha Sukthi Bhasma in an amount of ≤2 wt %, Shuddha gairika in an amount of ≤2 wt %, and Kapardika bhasma in an amount of ≤2 wt %, of the total weight of the composition. In another embodiment the composition includes Gandhaka in an amount in the range of 6 to 10 wt % of the total weight of the composition.

The Disclosed composition, in the various embodiments herein, may further include a suitable excipient. The list of suitable excipients may include solvents, binders, lubricants, herbal carriers, oils and salts that are generally known in the art. In an embodiment, the excipient includes acacia gum.

Further, the amount of herb and mineral that may be included in the various embodiments of the disclosed composition may each be in the range of 0 to 10 wt %. In an embodiment, the composition includes *Emblica officinalis* (6 to 10 wt %), *Terminalia chebula* (6 to 10 wt %), *Terminalia bellerica* (6 to 10 wt %), *Commiphora mukul* (6 to 10 wt %), *Azadirachta indica* (6 to 10 wt %), *Curcuma longa* (6 to 10 wt %) and Gandhaka (6 to 10 wt %), of the total weight of the composition.

In another embodiment, the composition includes *Emblica officinalis* (6 to 10 wt %), *Terminalia chebula* (6 to 10 wt %), *Terminalia bellerica* (6 to 10 wt %), *Commiphora mukul* (6 to 10 wt %), *Azadirachta indica* (6 to 10 wt %), *Curcuma longa* (6 to 10 wt %), *Piper longum* (≤2 wt %), *Solanum xanthocarpum* (≤2 wt %), *Tinospora cordifolia* (≤2 wt %), *Trichosanthes dioica* (≤2 wt %), *Holarrhena antidysenterica* (≤2 wt %), *Cyperus rotundus* (≤2 wt %), *Swertia chirata* (≤2 wt %), *Picrorhiza kurroa* (≤2 wt %), *Zingiber officinale* (≤2 wt %), *Piper nigrum* (≤2 wt %), *Alpinia galanga* (≤2 wt %), *Glycyrrhiza glabra* (≤2 wt %), *Acorus calamus* (≤2 wt %), *Oldenlandia corymbosa* (≤2 wt %) and Gandhaka (6 to 10 wt %), of the total weight of the composition.

In another embodiment, the composition includes *Emblica officinalis* (6 to 10 wt %), *Terminalia chebula* (6 to 10 wt %), *Terminalia bellerica* (6 to 10 wt %), *Commiphora mukul* (6 to 10 wt %), *Azadirachta indica* (6 to 10 wt %), Tankana Bhasma (≤2 wt %), Swarna makshika Bhasma (≤2 wt %), Muktha Sukthi Bhasma (≤2 wt %), Shuddha gairika (≤2 wt %), Kapardika bhasma (≤2 wt %), *Curcuma longa* (6 to 10 wt %) and Gandhaka (6 to 10 wt %).

In yet another embodiment, the composition includes *Emblica officinalis* (6 to 10 wt %), *Terminalia chebula* (6 to 10 wt %), *Terminalia bellerica* (6 to 10 wt %), *Commiphora mukul* (6 to 10 wt %), *Azadirachta indica* (6 to 10 wt %), *Curcuma longa* (6 to 10 wt %), *Piper longum* (≤2 wt %), *Solanum xanthocarpum* (≤2 wt %), *Tinospora cordifolia* (≤2 wt %), *Trichosanthes dioica* (≤2 wt %), *Holarrhena antidysenterica* (≤2 wt %), *Cyperus rotundus* (≤2 wt %), *Swertia chirata* (≤2 wt %), *Picrorhiza kurroa* (≤2 wt %), *Zingiber officinale* (≤2 wt %), *Piper nigrum* (≤2 wt %), *Alpinia galanga* (≤2 wt %), *Glycyrrhiza glabra* (≤2 wt %), *Acorus calamus* (≤2 wt %), *Oldenlandia corymbosa* (≤2 wt %), Tankana Bhasma (≤2 wt %), Swarna makshika Bhasma (≤2 wt %), Muktha Sukthi Bhasma (≤2 wt %), Shuddha gairika (≤2 wt %), Kapardika bhasma (≤2 wt %) and Gandhaka (6 to 10 wt %), of the total weight of the composition; and a suitable excipient. In an embodiment, the suitable excipient is acacia gum.

Further, the amount of gum acacia may be any amount suitable to perform the activity of an excipient. In an embodiment, the composition may include gum acacia in an amount in the range of 8 to 12 wt %.

However, it is apparent that slight variations in the amount of the ingredients may be accommodated without otherwise deterring from the intended function of the composition.

The herbal composition disclosed herein may be formulated in various dosage forms such that it is suitable for oral administration. The herbal composition may be in the form of tablets, pellets, lozenges, granules, capsules, solutions, emulsions, suspensions, or any other form suitable for use. In an embodiment, the herbal composition is formulated in the form of tablets, preferably 500 mg tablets. For example: Table 1A depicts the quantities of each ingredient in a 500 mg tablet. All weight percentages provided herein are based on the total weight of the composition.

Further disclosed herein, is a tablet for treating infectious diseases. In an embodiment, the tablet is a 500 mg tablet having herb component, mineral component and excipient as depicted in Table 1.

TABLE 1

Each 500 mg tablet includes:

| Sl. No. | Sanskrit Name | Latin/English name | Quantity |
|---|---|---|---|
| 1. | Amalaki | Emblica officinalis | 40 mg |
| 2. | Hareetaki | Terminalia chebula | 40 mg |
| 3. | Vibhitaki | Terminalia bellerica | 40 mg |
| 4. | Guggulu | Commiphora mukul | 40 mg |
| 5. | Nimba | Azadirachta indica | 40 mg |
| 6. | Haridra | Curcuma longa | 40 mg |
| 7. | Pippali | Piper longum | 10 mg |
| 8. | Kantakari | Solanum xanthocarpum | 10 mg |
| 9. | Guduchi | Tinospora cordifolia | 10 mg |
| 10. | Patola | Trichosanthes dioica | 10 mg |
| 11. | Kutaja | Holarrhena antidysenterica | 10 mg |
| 12. | Mustaka | Cyperus rotundus | 10 mg |
| 13. | Kiratha | Swertia chirata | 10 mg |
| 14. | Katuki | Picrorhiza kurroa | 10 mg |
| 15. | Shunti | Zingiber officinale | 10 mg |
| 16. | Maricha | Piper nigrum | 10 mg |
| 17. | Rasna | Alpinia galanga | 10 mg |
| 18. | Yastimadhu | Glycyrrhiza glabra | 10 mg |
| 19. | Vacha | Acorus calamus | 10 mg |
| 20. | Parpata | Oldenlandia corymbosa | 10 mg |
| 21. | Tankana Bhasma | Dehydrated borax | 5 mg |
| 22. | Gandhaka | Sulfur | 40 mg |
| 23. | Swarna makshika Bhasma | Calx of copper pyrite | 5 mg |
| 24. | Muktha Sukti Bhasma | Calx of Pearl oyster | 5 mg |
| 25. | Shuddha gairika | Hematite | 10 mg |
| 26. | Kapardika bhasma | Calx of cowries | 5 mg |
| 27. | Excipient | Gum acacia | 50 mg |

In an embodiment, the disclosed composition is a blackish brown biconvex shaped tablet having the characteristics as depicted in Table 2. The invention is further described by reference to the following table by way of illustration only, and should not be construed to limit the scope of the present invention. It will be apparent to those skilled in the art that many modifications may be practiced without departing from the scope of the present invention.

TABLE 2

| Test Parameters | Specifications |
|---|---|
| Description | Blackish brown biconvex shaped tablets |
| Identification | Tests positive for iron and calcium. |
| Average weight | 500 mg ± 12.5 mg (Average wt. 514 mg) |
| Uniformity of weight | ±2.5% of actual average weight |
| Average tablet hardness | 2.2 kg/cm$^2$ |
| pH in 10% aqueous solution | 3.7 |
| Loss on drying | 8.5% w/w |

TABLE 2-continued

| Test Parameters | Specifications |
|---|---|
| Methanol soluble extractive | 21.03% w/v |
| Chloroform soluble extractive | 4.16% w/v |
| Ash value | 6.0% w/w |
| Acid insoluble ash | 0.5% w/w |
| Average Tablet Disintegration time | 20 minutes |
| Assay: | |
| Tannin content | 3011% |
| Ascorbic acid | 0.25% |

Each tablet contains, iron: 2.90 mg, calcium: 7.7 mg
TLC of alcoholic extract of the drug in silica gel "G" plate using Toluene: Ethyl acetate (9:1) shows under UV light(366 nm), 8 spots of RF. 0.02 (yellow), 0.12 (light green), 0.25 (green), 0.31 (light green), 0.36 (light green), 0.53 (light green), 0.53 (green) and 0.67 (blue).

Method

Disclosed herein are embodiments of a method of preparing the herbal composition. In an embodiment, the method includes, levigating processed bhasma, Shuddha gairika and Gandhaka in a grinder;

adding finely powdered herbs and grinding decoction into the grinder while continuing grinding;

adding fresh juice of herbs while continuing grinding to obtain a ground mass; and mixing guggulu with grinding decoction and adding it to the ground mass to obtain the composition.

In another embodiment, the process further includes mixing an excipient such as gum acacia with guggulu and grinding decoction and grinding for a period of 1 to 3 hours; and drying of the obtained mass at a temperature in the range of 40 to 60 degree Celsius. Further, the obtained mass may be subjected to wet granulation followed by punching into 500 mg tablets.

The bhasmas include at least one of Tankana Bhasma, Swarna makshika Bhasma, Muktha Sukthi Bhasma and Kapardika bhasma. The mixture of bhasma, Shuddha gairika and Gandhaka may be in semi solid form. In an embodiment, the levigation may be performed for a duration of around 3 hours.

Further, the finely powdered herbs include finely powdered dry fruits of Emblica officinalis, Terminalia chebula and Terminalia bellerica; dry stem bark of Azadirachta indica; and dry rhizome of Curcuma longa.

The finely powdered herbs may further include finely powdered dry fruits of Piper longum and Piper nigrum; stem bark of Holarrhena antidysenterica; rhizome of Acorus calamus and Zingiber officinale; whole plant of Solanum xanthocarpum, Oldenlandia corymbosa, Trichosanthes dioica and Swertia chirata; stem of Tinospora cordifolia; tuber of Cyperus rotundus; roots of Picrorhiza kurroa, Alpinia galanga and Glycyrrhiza glabra. In an embodiment, finely powdered herbs may be obtained by powdering and sieving the herb components at 80 mesh.

The grinding decoction is a decoction of herbs (also referred to as grinding herbs) that may facilitate grinding. In an embodiment, the grinding decoction includes a decoction of at least one herb selected from a list consisting of: Embilca officinalis, Terminalia chebula, Terminalia bellerica, Aloe vera, Asparagus racemosus, Swertia chirata, Steriospermum suaveolens, Premna mucronate, Gmelina arborea, Aegle marmelos, Oroxylum indicum, Desmodium gangeticum, Uraria picta, Solanum indicum, Solanum xanthocarpum, Tribulus terrestris, Adhatoda vasica, Phyllanthus niruri, Ocimum sanctum, Ricinus communis and Plumbago rosea.

The decoction may be obtained by any method of decocting generally known in the field. In an embodiment, the method of preparation of grinding decoction includes:

soaking the grinding herbs. For example, soaking powdered dry fruit of Embilca officinalis, dry fruit of Terminalia chebula, dry fruit of Terminalia bellerica, fresh leaves of Aloe vera, fresh roots of Asparagus racemosus, fresh whole plant of Swertia chirata, dry roots of Steriospermum suaveolens, dry roots of Premna mucronate, dry roots of Gmelina arborea, dry roots of Aegle marmelos, dry roots of Oroxylum indicum, dry plant of Desmodium gangeticum, dry plant of Uraria picta, dry roots of Solanum indicum, dry plant of Solanum xanthocarpum, dry fruit of Tribulus terrestris, dry roots of Adhatoda vasica, whole plant of Phyllanthus niruri, fresh leaves of Ocimum sanctum, dry roots of Ricinus communis and purified dry roots of Plumbago rosea; and concentrating the soaked herb mixture.

In an embodiment, soaking may be performed by soaking the grinding herbs in 16 parts of water overnight. In a further embodiment, concentrating may be performed by boiling at high temperature, preferably about 80° C. to 85° C., until ⅛th of the liquid remains. Concentration may be confirmed with the help of Brix meter.

Further, once the grinding decoction is added grinding is continued. In an embodiment, grinding is continued for about 72 hours, preferably at about 120 rpm. The grinding decoction is a decoction of herbs (also referred to as grinding herbs) that may facilitate grinding. In an embodiment, the fresh juice of herbs includes at least one fresh juice selected from a list consisting of: Dhattura Rasa, Bhringaraja Rasa, Tulasi Rasa and Ardraka Rasa.

In an embodiment, the fresh juice Dhattura Rasa, Bhringaraja Rasa, Tulasi Rasa and Ardraka Rasa is added one at a time while continuing grinding to obtain a ground mass, wherein grinding is done at 120 rpm for 72 hours after adding every juice.

Further, Guggulu is added to the composition (or ground mass) by mixing with the grinding decoction while continuing grinding. In an embodiment, the grinding is continued for a period of 1 to 3 hours. In an embodiment, the grinding is continued for a period of 3 hours.

Figure 2:
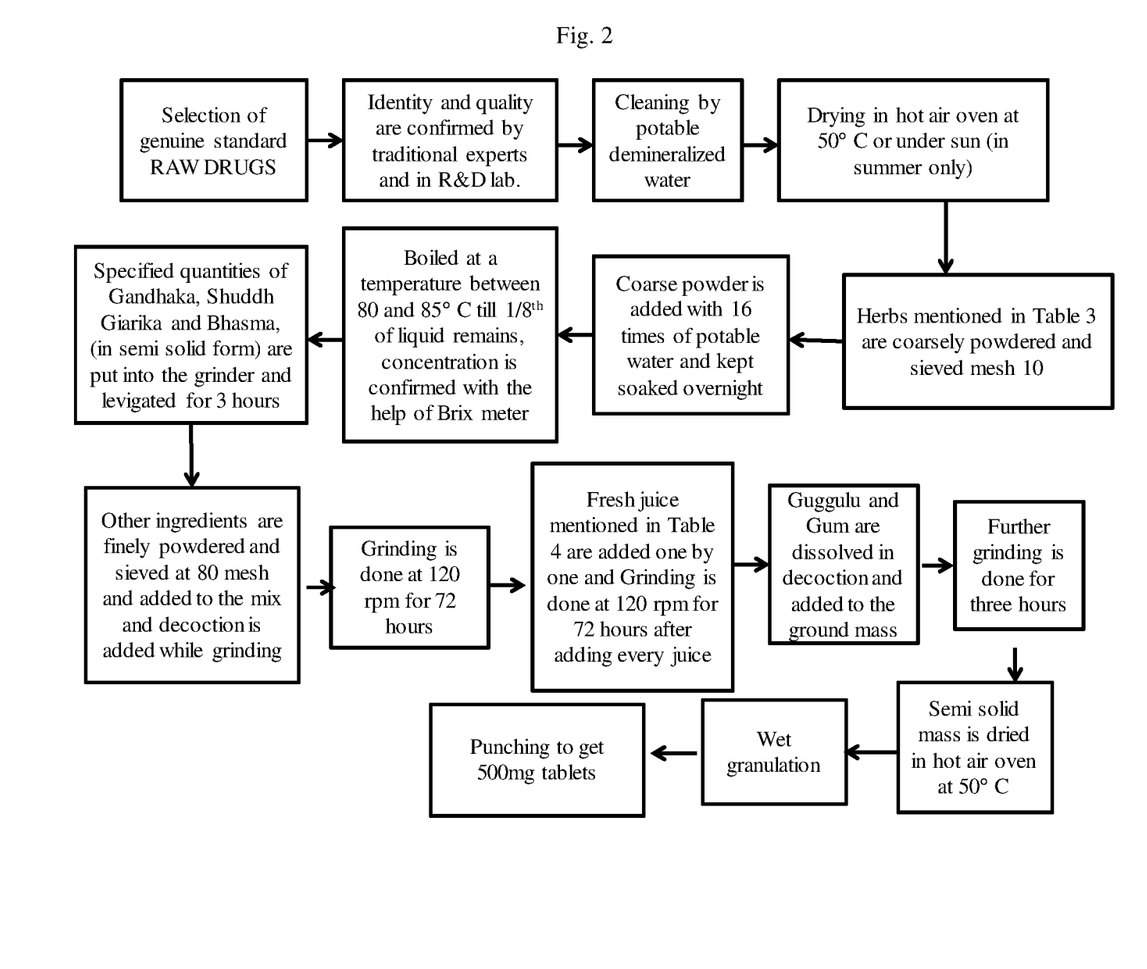
FIG. 2 depicts a flowchart for the preparation of fortified tablets, according to embodiments as disclosed herein.

In another embodiment, gum acacia is also mixed with Guggulu and grinding decoction which is further added to the ground mass while continuing grinding for 3 hours to obtain a semisolid mass. In another embodiment, the method further includes drying the obtained mass at about 50 degree Celsius, preferably in a hot air oven, to obtain a composition disclosed in the various embodiments herein. In another embodiment, the method may further include wet granulating and punching of the obtained mass to obtain 500 mg tablets. FIG. 2 depicts a flowchart for the preparation of fortified tablets. Table 3 depicts the Herb ingredients used to prepare grinding decoction required for grinding (grinding herbs) in one of the preferred embodiments.

TABLE 3

Decoction of following herbs:

|  |  |  |  |
|---|---|---|---|
| 1. | Amalaki dry fruits | Emblica officinalis | 1 part |
| 2. | Hareetaki dry fruits | Terminalia chebula | 1 part |
| 3. | Vibhitaki dry fruits | Terminalia bellerica | 1 part |
| 4. | Kumari fresh leaf | Aloe vera | 1 part |
| 5. | Shatavari fresh root | Asparagus racemosus | 1 part |
| 6. | Kiratatikta fresh whole plant | Swertia chirata | 1 part |
| 7. | Patala dry root | Steriospermum suaveolens | 1 part |
| 8. | Agnimantha dry root | Premna mucronata | 1 part |
| 9. | Gambhari dry root | Gmelina arborea | 1 part |
| 10. | Bilva dry root | Aegle marmelos | 1 part |
| 11. | Shyonaka dry root | Oroxylum indicum | 1 part |
| 12. | Shalaparni dry plant | Desmodium gangeticum | 1 part |
| 13. | Prshniparni dry plant | Uraria picta | 1 part |
| 14. | Brhati dry root | Solanum indicum | 1 part |
| 15. | Kantakari dry plant | Solanum xanthocarpum | 1 part |
| 16. | Gokshura dry fruit | Tribulus terrestris | 1 part |
| 17. | Vasa dried root | Adhatoda vasica | 1 part |
| 18. | Boomyamalaki whole plant | Phyllanthus niruri | 1 part |
| 19. | Tulasi fresh leaves | Ocimum sanctum | 1 part |
| 20. | Eranda dried root | Ricinus communis | 1 part |
| 21. | Chitraka purified dried root | Plumbago rosea | 1 part |
|  | Jala | Water | 336 parts |
|  | Avashesha (Reduced to) |  | ⅛ part of water |

Table 4 depicts the Herb ingredients used in the form of fresh juice that is required for grinding in one of the preferred embodiments.

TABLE 4

Fresh juice of following herbs:

|  |  |  |  |
|---|---|---|---|
| 1. | Dhattura Rasa | Juice of fresh leaves | 1 part |
| 2. | Bhringaraja Rasa | Juice of fresh plant | 1 part |
| 3. | Tulasi Rasa | Juice of fresh leaves | 1 part |
| 4. | Ardraka Rasa | Juice of fresh rhizome | 1 part |

The bhasmas that are used in the various embodiments of the disclosed herbal composition may be prepared by methods that are generally known in the field. Bhasmas may be prepared by selecting genuine standard minerals as starting material such as Swarna makshika, Peral oyester, borax etc; drying in a hot air oven; purifying the mineral by triturating, quenching, boiling, etc.; triturating the purified material with herbal decoction/juice; preparing into discs; drying of discs; preparing sharavasam puta, subjecting Sharavasam puta to Gaja puta, and powdering of discs once cooled. In an embodiment, the method is repeated 30 times till bhasma is obtained.

Figure 1A:
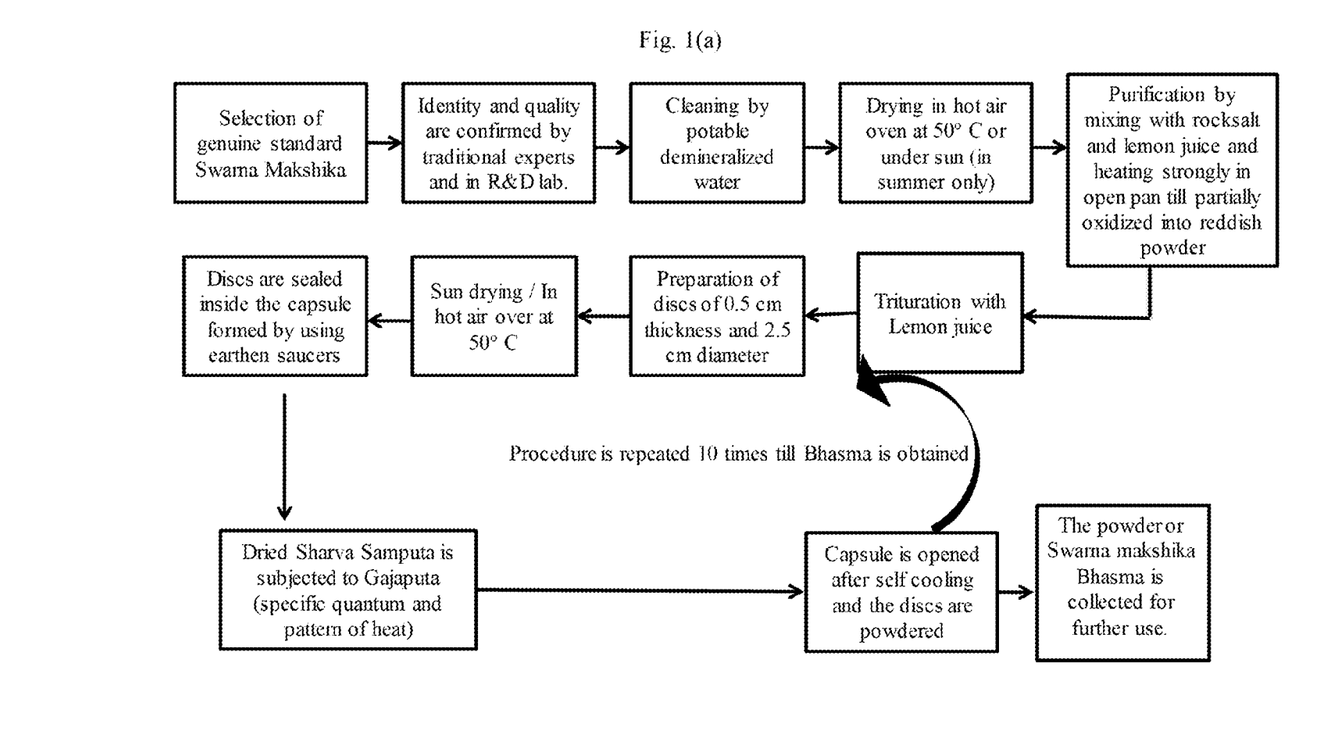
FIG. 1(a) depicts a flowchart for the preparation of Swarna Makshika Bhasma, according to embodiments as disclosed herein.
Figure 1B:
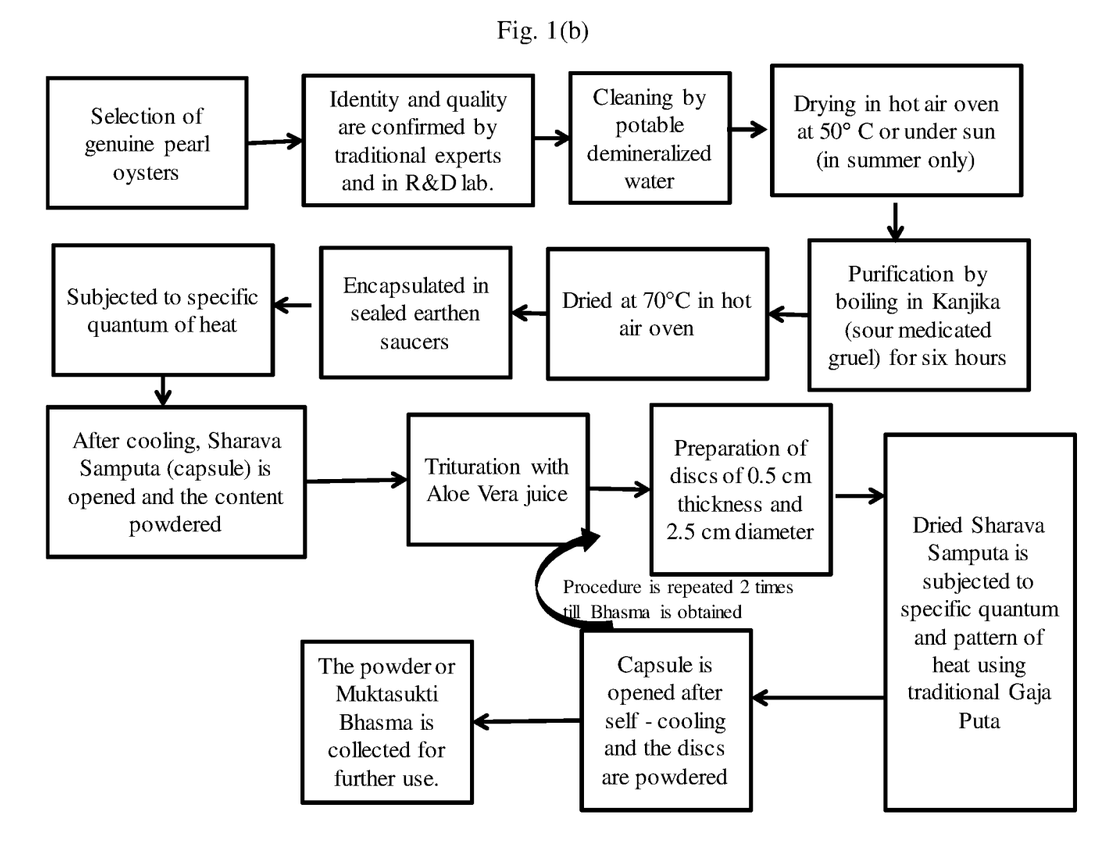
FIG. 1(b) depicts a flowchart for the preparation of *Mukta Sukti Bhasma*, according to embodiments as disclosed herein.
Figure 1C:
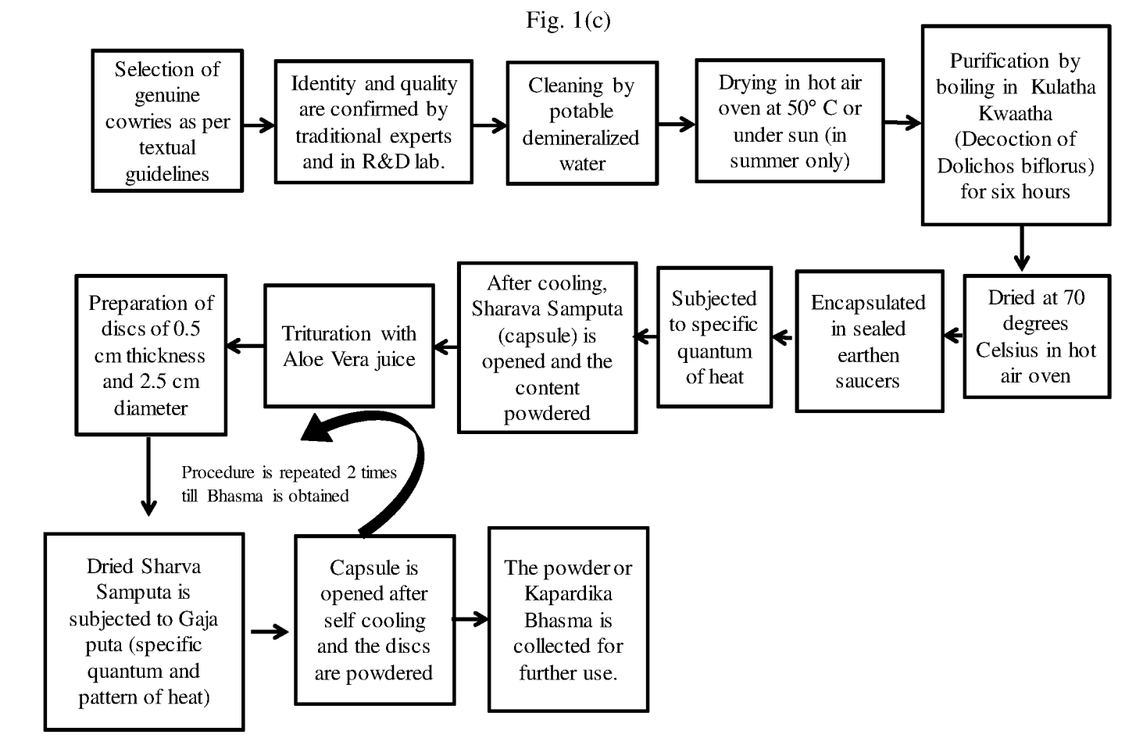
FIG. 1(c) depicts a flowchart for the preparation of Kapardika Bhasma, according to embodiments as disclosed herein.
Figure 1D:
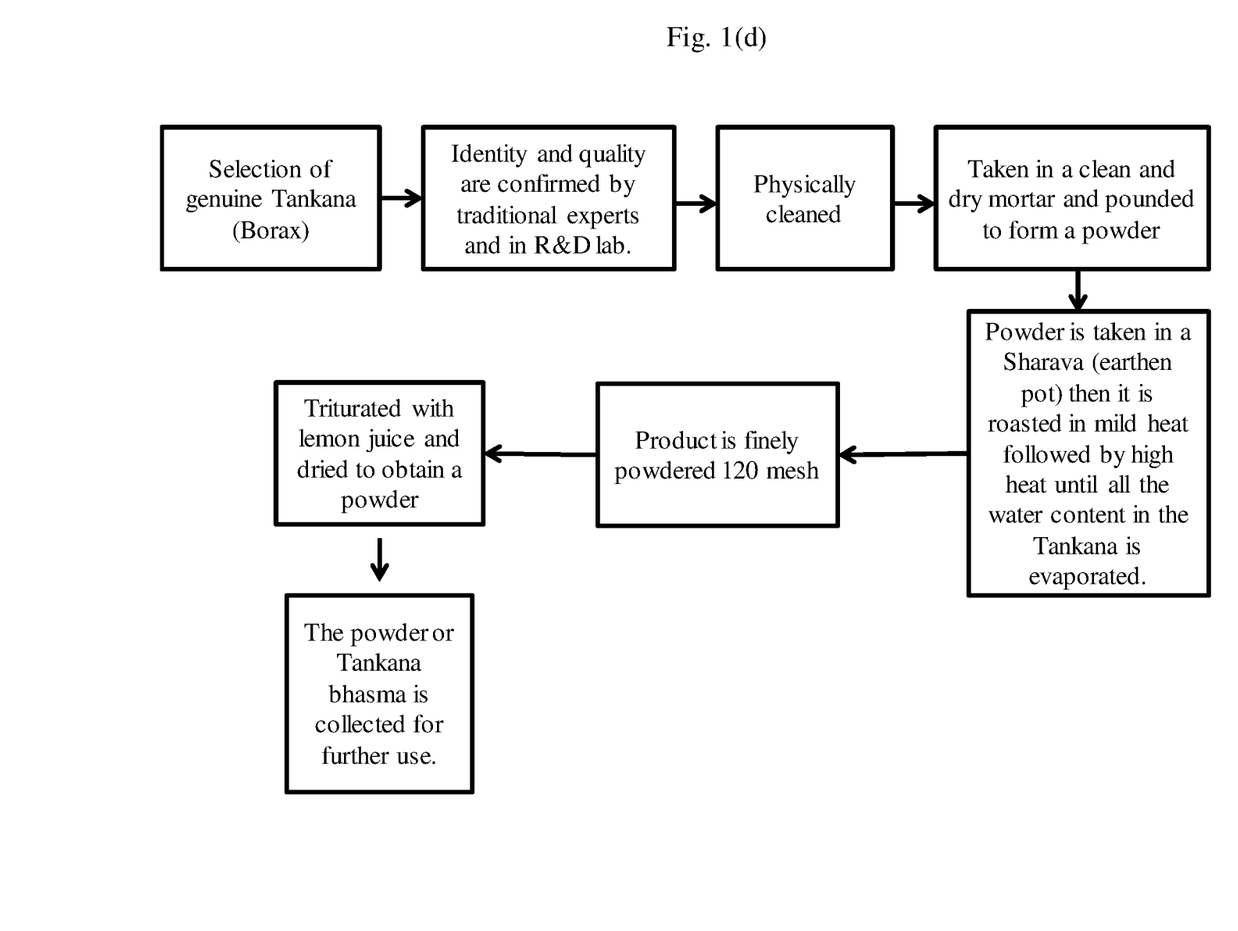
FIG. 1(d) depicts a flowchart for the preparation of *Tankana Bhasma*, according to embodiments as disclosed herein.

The starting materials used in the preparation of bhasmas may include standard minerals generally used in the field. In an embodiment, the preparation of Swarna makshika Bhasma includes Swarna makshika (Chalcopyrite) as the starting material. FIG. 1(a) depicts a flowchart for the preparation of Swarna makshika Bhasma using Swarna makshika as the starting material. In an embodiment, the preparation of *Mukta* sukti bhasma includes pear oyester as the starting material. FIG. 1(b) depicts a flowchart for the preparation of *Mukta* sukti bhasma using pearl oyester as the starting material. In an embodiment, the preparation of Kapardika Bhasma includes Cowries as the starting material. FIG. 1(c) depicts a flowchart for the preparation of Kapardika Bhasma using cowries as the starting material. In another embodiment, the preparation of Tanaka Bhasma includes Borax as the starting material. FIG. 1(d) depicts a flowchart for the preparation of Tanaka Bhasma using Borax as the starting material.

The purification, or shodhana, of the mineral may be performed by generally known methods in the field. In an embodiment, the purification is by mixing the starting material with rock salt and lemon juice such as that in the preparation of Swarna makshika Bhasma. In another embodiment, the purification is by boiling in Kanjika (sour medicated gruel) such as that in the preparation of Muktasukti Bhasma. In another embodiment, the purification is by boiling in Kulattha Kwatha (decoction of *Dolichos biflorus*) such as that in the preparation of Kapardika Bhasma. In yet another embodiment, the purification is by roasting in an earthen pot (sharava) under mild heat followed by high heat, preferably until the water evaporates, such as that in the preparation of Tanaka Bhasma.

The herbal decoction/juice used may be any herbal decoction/juice that is generally used for triturating in the preparation of bhasmas. For example, the herbal decoction/juice may include triphala, lemon juice, Gomutra (cow's urine) etc. In an embodiment, the herbal decoction/juice used in the preparation of Swarna Makshika bhasma and Tanaka bhasma specifically includes Nimbu Swarasa (Lemon juice). In another embodiment, the herbal decoction used in the preparation of *Mukta* Bhasma and Kapardika bhasma specifically includes *Aloe vera* juice.

Embodiments are further described herein by reference to the following examples. The following examples are included herein by way of illustration only and should not be construed to limit the scope of the claims provided herewith.

Treatment

Disclosed herein are embodiments of a method of treatment and management of Infectious diseases. In the various embodiments herein, Infectious diseases shall include any condition generally known to be infectious. Infectious diseases in the various embodiments include conditions arising from Infections of Gram negative bacteria, Gram positive bacteria, fungus, viral etc. Infectious diseases may also further include respiratory disorders such as Pharyngitis, Laryngitis, Bronchitis, etc. Accordingly, embodiments disclosed herein include a method for treatment and management of respiratory disorders such as Pharyngitis, Laryngitis, Bronchitis etc.

In an embodiment, the method includes administering a patient with the composition as described in any of the embodiments disclosed herein. The patient according to the various embodiments herein may include any individual in need of such treatment including but not limited to individuals having Infectious diseases. The patient may further include any individual having infections of Gram negative bacteria, Gram positive bacteria, fungus, viral, bacterial etc. Further, the patient may also be any individual having respiratory disorders such as Pharyngitis, Laryngitis, Bronchitis, etc. Furthermore, the patient may also include individuals having symptoms associated with infectious diseases.

In another embodiment, the method includes administering to a patient a composition having *Emblica officinalis* (6 to 10 wt %), *Terminalia chebula* (6 to 10 wt %), *Terminalia bellerica* (6 to 10 wt %), *Commiphora mukul* (6 to 10 wt %), *Azadirachta indica* (6 to 10 wt %), *Curcuma longa* (6 to 10 wt %), *Piper longum* (≤2 wt %), *Solanum xanthocarpum* (≤2 wt %), *Tinospora cordifolia* (≤2 wt %), *Trichosanthes dioica* (≤2 wt %), *Holarrhena antidysenterica* (≤2 wt %), *Cyperus rotundus* (≤2 wt %), *Swertia chirata* (≤2 wt %), *Picrorhiza kurroa* (≤2 wt %), *Zingiber officinale* (≤2 wt %), *Piper nigrum* (≤2 wt %), *Alpinia galanga* (≤2 wt %), *Glycyrrhiza glabra* (≤2 wt %), *Acorus calamus* (≤2 wt %), *Oldenlandia corymbosa* (≤2 wt %), Tankana Bhasma (≤2 wt %), Swarna makshika Bhasma (≤2 wt %), Muktha Sukthi Bhasma (≤2 wt %), Shuddha gairika (≤2 wt %), Kapardika bhasma (≤2 wt %), Gandhaka (6 to 10 wt %); and a suitable excipient.

In an embodiment, the disclosed composition may also be used to prevent Infectious diseases.

The patient may be administered a therapeutically effective amount of the embodiments of the disclosed composition. The therapeutically effective amount may vary depending on the patient. In an embodiment, the therapeutically effective amount is 500 to 1000 mg administered one to three times a day. Embodiments of the disclosed composition (also referred as Test drug or product) were tested for safety and efficacy, as described hereunder by way of examples. Embodiments are described herein by reference to the following examples by way of illustration only and should not be construed to limit the scope of the claims provided herewith.

Example 1: Safety Study

Test drug was administered once orally to overnight fasted female Wistar rats at 2000 and 5000 mg/kg body weight (2 steps/dose; 3 animals/step) at a dose volume 10 ml/kg. Body weight was recorded on day 0, 7 and 14. Mortality/Clinical signs were observed at approximately 30 minutes, 1, 2 and 4 h on day 0 (after test item administration) and thereafter once daily for 14 days.

All the experimental animals showed gain in body weight on day 7 and 14 in comparison to their day 0 body weight. No clinical signs and mortality were observed for 14 days in all experimental animals. No gross lesions were detected in animal treated with 2000 mg/kg body weight, whereas in animal number 8, treated with 5000 mg/kg body weight shows multifocal point of congestion in lungs. No gross lesions were detected in all other organs of experimental animals treated with 5000 mg/kg body weight.

Histopathologic examination of lungs of animal number 8 revealed alveolar hemorrhages, alveolar thickening with mononuclear cells infiltration and multifocal aggregates of mixed population of inflammatory cells around blood vessels and bronchioles.

Based on the above observations, the LD50 value of "Test drug" was found to be greater than 5000 mg/kg body weight and classified as Category-5 or unclassified based on Globally Harmonised Classification System (GHS) for Chemical Substances and Mixtures.

Example 2: Efficacy Study

2a. Antimicrobial study
2b. Clinical study

Example 2a: Antimicrobial Study

Abstract

Antimicrobial agents are commonly used nowadays for treating various bacterial and fungal infections. But still most of the physicians are unable to treat these infections appropriately due to hindrances like development of resistance, adverse effects, patient affordability etc. Test drug developed can be an ideal replacement for treating various infectious diseases. Assessment of its antibacterial and antifungal activity may provide scientific evidence for the study. Test drug is evaluated against multiple strains of gram positive and gram negative bacteria and selected fungal strains. Disc diffusion method was followed. The results showed highly efficient antimicrobial effect of test drug against multiple strains, especially *Salmonella typhi, Salmonella typhimurium, E. Coli* and *Staphylococcus aureus*

Introduction

Antimicrobial activities of any therapeutic agent are understood by its degree of growth inhibition of microorganisms as well as bacterial property. Usually different microbial species and strains have different degrees of susceptibility to therapeutic agents. The susceptibility of microorganisms can change with time even during therapy with a specific drug. Thus, it is essential for the physician to know the sensitivity of the pathogen before treatment. In present study the antibiotic, antibacterial and antifungal effect of test drug is evaluated.

Antimicrobial study: The antimicrobial activity of a drug is generally expressed as its inhibiting effect toward the growth of the bacterium in nutrient broth or nutrient agar.

For this study, the following conditions are required:
1. The substance or test drug must be in contact with the test organisms.
2. Conditions must be favorable for the growth of microorganisms in the absence of antimicrobial substances.
3. There must be a means of estimating the amount of growth and thereby percentage of growth of inhibition.
4. The activity of test drug should be observed and determined by the growth response of microorganisms.

Bacterial Strain Used—

Gram negative Strain—*Escherichia coli* (NCIM 2574) and *Pseudomonas aeruginosa* (NCIM 2036); Gram positive Strain—*Staphylococcus aureus* (NCIM 2079); Fungal Strain—*Candida albicans*.

Media Used—

Mueller Hinton agar, Mueller Hinton broth, Sabouraud dextrose broth and Sabouraud dextrose agar.

Standard Drug Disc—

Gentamycin (10 µg/disc) for Gram negative; Ampicillin (10 µg/disc) for Gram positive; Amphotericin B (20 µg/disc) for fungi Procedure:

Preparation of Inocula:

For preparation of inoculum, growth from the agar slant was scrapped by adding 3 ml of sterile saline solution. This saline cell suspension was then spread evenly on large sterile Petri plates containing solidified Muller Hinton agar (for bacteria) and Sabouraud dextrose agar (for fungi) using a sterile glass spreader. These plates were incubated in bacteriological incubator at 37° C. for 24 hours and at 28° C. for 48 hours for bacteria and fungi respectively. After profuse growth of the organism in the Petridish, it was scrapped using sterile spatula and adding small portion of sterile saline. This suspension was transferred to a sterile 100 ml conical flask. The final volume of the suspension was made upto 50 ml with sterile saline.

Standardization of Inocula:

For determination of MIC, the inoculum density was adjusted to contain $5 \times 10^6$ CFU/ml which have turbidity equal to 0.5 McFarland standard. For this, 0.5 McFarland standard was prepared by adding 0.05 ml of 0.048M $BaCl_2$ (1.17% w/v $BaCl_2.2H_2O$) to 9.95 ml of 0.18M $H_2SO_4$ (1% w/v) with constant stirring. The standard was transferred to a glass screw capped bottle.

Absorbance of the McFarland standard was checked at 625 nm (absorbance at 625 nm should range between 0.08-0.13).

Preparation of Drug Dilution:

Each drug was suspended in sterile water with the help of 1% tween 80 at the concentration of 1 mg/ml. sterile water with 1% tween 80 was also prepared to use a blank for the drug. Test drug tablet was powdered and made into suspension.

Disk Diffusion Assay:

Disk diffusion assay of drug was performed in 40 mm Petri plates to observe growth inhibition of test organism in term of zone of diameter (mm). Mueller Hinton agar (3 in No.) and Sabouraud dextrose agar (1 in No.) medium was prepared and sterilized. Molten agar media were poured in sterile Petri plates (4 in No.) and left for Solidification. Each plate was neatly labeled with all the details. Standard cultures (100 µl of each) of test organism were transferred on the respected solidified agar aseptically. Transferred cultures were uniformly distributed all around the surface of agar medium using L spreader. Respected standard was kept in the center of respected part of the plate. Three sterile discs were transferred into the remaining parts of the plate. Each sterile disc was loaded with the 20 µl of respected drug or blank. First, Petri plates were kept in fridge for 30 min. for drug diffusion and then transferred into the respective incubator. Zones of inhibition were measured using antibiotic zone reader after 24 h for bacteria and 48 h for fungi. Table 5 depicts the results of antibacterial assay of Test drug. Table 6 depicts the results of antifungal assay of Test drug.

TABLE 5

Report of antibacterial assay of Test drug

| | Zone Diameter (mm) of Growth Inhibition | | |
|---|---|---|---|
| Name of tested organism | Test drug | Blank | Standard drug |
| Salmonella typhi | 38 | 9 | 21 |
| Salmonella typhimurium | 40 | 8 | 32 |
| E. Coli | 36 | — | 24 |
| Staphylococcus aureus | 38 | — | — |
| Proteus | 29 | — | 24 |
| Pseudomonas aeruginosa | 28 | — | 26 |
| Staphylococcus epidermidis | 26 | — | 28 |

TABLE 6

| | Report of antifungal assay of Test drug | | |
|---|---|---|---|
| Name of | Zone Diameter (mm) of Growth Inhibition | | |
| tested organism | Test drug | Blank | Standard drug |
| C. albicans | 15 | — | 8 |

Results:

Test drug was found to be highly active against used Gram negative and Gram positive bacteria at tested concentration. It was also found to be active against fungal strain.

Conclusion

Test drug was found to be highly active against used Gram negative and Gram positive bacteria at tested concentration. It was also found to be active against fungal strain. Most potent activity was observed against the bacterial strains *Salmonella typhi, Salmonella typhimurium, E. Coli* and *Staphylococcus aureus*

Example 2b: Clinical Study

Clinical Evaluation of Test drug tablets in Chronic Pharyngitis

Introduction: Chronic pharyngitis may be sometimes due to some primary infection in the pharyngeal tissue itself but most of the time it is secondary to diseases in other parts of the upper respiratory tract or some other systems. The nose, sinuses, teeth and tonsils act as reservoirs of infection and the pharynx is the victim all the time.

Environmental population especially in industrial areas predisposes to this condition. Fumes, gases, chemicals, smoke and a dust-laden atmosphere are the common factors in modern cities and towns, thus increasing the incidence and chronicity of this condition.

A constant feeling of soreness and discomfort as well as pain and a sensation of a foreign body, irritable cough and a tired voice are the main symptoms. Frequent desire to clear the cough makes the condition even worse.

In spite of the best of treatments for both local and secondary causes, this problem continues to be a challenge to the otolaryngologists. Sometimes post-tonsillectomy and adenoidectomy cause hypertrophic pharyngitis and a dry irritating cough which are very resistant to all sorts of treatment ranging from chemical cauterization to antibiotics and antiallergics. Keeping this in view, this trial has been undertaken and only those cases have been selected who had been previously treated for both primary and secondary causes, but without success. As antibiotics may not be used for longer periods, Test drug, an indigenous remedy, has been tried with some antihistamines for longer periods and the results have been evaluated.

Material and Methods:

Twenty eight cases of chronic pharyngitis were selected for the study. Their age, sex and symptoms were noted (See Tables I, II and III). A thorough clinical examination was done and routine tests were carried out. Wherever necessary, special tests were also done. Test drug was given for 6-8 weeks in the doses of 1 tablet b.i.d. in children below 12 years of age and 2 tablets b.i.d. in those above 12 years. They were asked to report to the OPD every fifteenth day when their symptoms and signs were assessed. The response to treatment was judged by the improvement in symptoms and was graded in three categories.

(a) Good—Where most of the symptoms showed complete cessation during treatment and remained absent for the next 3 months.
(b) Fair—Where most of the symptoms were absent during treatment but were reported before the next 6 months.
(c) Poor—Where most of the symptoms persisted even during treatment.

Table 7 is a tabulation depicting the percentage age of incidence. It shows that the maximum number of cases were reported in the age group of 21-30 years—they were 12 or 42.86% of the total. Next in order was the age group from 11 to 20 years (17.86%), next are of the age group 31 to 40 years and 40 years onwards (14.28% each). The least number of cases came from the youngest age group of 0-10 years (10.71%).

TABLE 7

| | Age incidence (Years) | | | | | | | | | |
|---|---|---|---|---|---|---|---|---|---|---|
| Total No. | 0-10 | | 11-20 | | 21-30 | | 31-40 | | 40 onwards | |
| of cases | No. | % | No. | % | No. | % | No. | % | No. | % |
| 28 | 3 | 10.71 | 5 | 17.86 | 12 | 42.86 | 4 | 14.28 | 4 | 14.28 |

Table 8 depicts the percentage incidence based on sex. It shows the sex incidence to be more in females, 53.57% and those in males 46.43%.

TABLE 8

| | Sex incidence (Years) | | | |
|---|---|---|---|---|
| | Males | | Females | |
| Total No. of cases | No. | % | No. | % |
| 28 | 13 | 46.43 | 15 | 53.57 |

Table 9 depicts the criteria for grading the results.

| S. No. | Relief of Symptoms | Good | Fair | Poor |
|---|---|---|---|---|
| 1. | Soreness | Complete cessation | Complete cessation | Improvement |
| 2. | Discomfort | Complete cessation | Persists | Improvement |
| 3. | Feeling of foreign body presence | Complete cessation | Complete cessation | Improvement |
| 4. | Pain | Complete cessation | Complete cessation | No response |
| 5. | Irritable cough | Complete cessation | Complete cessation | Diminished in intensity |
| 6. | Tiredness in voice | Complete cessation | Complete cessation | Improvement |

Table 10 depicts the results obtained during the evaluation. Fourteen out of 28 cases (50%) showed good results, that means they were free from all symptoms during the treatment and for the next three months at least. A good number of cases i.e. 13 out of 28 (46.43%) showed fair response. Most of the symptoms were absent during the treatment but re-appeared within 3 months after cessation of treatment. One patient showed poor response with this remedy: some of the symptoms did not improve even during treatment and recurrence was frequent.

| Total no. of cases | Results | | | | | |
|---|---|---|---|---|---|---|
| | Good | | Fair | | Poor | |
| | No. | % | No. | % | No. | % |
| 28 | 14 | 50 | 13 | 46.43 | 01 | 3.57 |

Its long-term use was devoid of any side-effects. Patients not improving on conventional antibiotics showed improvement with this remedy.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. A composition for treatment and management of infectious disease, comprising a therapeutically effective amount of *Emblica officinalis* or its extract, *Terminalia chebula* or its extract, *Terminalia bellerica* or its extract, *Commiphora mukul* or its extract, *Azadirachta indica* or its extract, *Curcuma longa* or its extract; and at least one other ingredient selected from a group consisting of Gandhaka, Shuddha Gairika and Bhasma, wherein said Bhasma is at least one Bhasma selected from a group consisting of *Tankana Bhasma*, Swarna makshika Bhasma, *Mukta Shukti* Bhasma and Kapardika bhasma.

2. The composition as claimed in claim 1, wherein said *Emblica officinalis* is present in an amount ranging from 6 to 10 wt % of the total weight of the composition; *Terminalia chebula* is present in an amount ranging from 6 to 10 wt % of the total weight of the composition; *Terminalia bellerica* is present in an amount ranging from 6 to 10 wt % of the total weight of the composition; *Commiphora mukul* is present in an amount ranging from 6 to 10 wt % of the total weight of the composition; *Azadirachta indica* is present in an amount ranging from 6 to 10 wt % of the total weight of the composition; and *Curcuma longa* is present in an amount ranging from 6 to 10 wt % of the total weight of the composition.

3. The composition as claimed in claim 1, wherein said Gandhaka is present in an amount ranging from 6 to 10 wt % of the total weight of the composition.

4. The composition as claimed in claim 1, wherein said Shuddha Gairika is present in an amount of ≤2 wt % of the total weight of the composition.

5. The composition as claimed in claim 1, wherein said bhasma is Swarna Makshika bhasma present in an amount of ≤2 wt % of the total weight of the composition.

6. The composition as claimed in claim 1, wherein said bhasma is *Tankana Bhasma* present in an amount of ≤2 wt % of the total weight of the composition.

7. The composition as claimed in claim 1, wherein said bhasma is *Mukta Shukti* bhasma present in an amount of ≤2 wt % of the total weight of the composition.

8. The composition as claimed in claim 1, wherein said bhasma is Kapardika bhasma present in an amount of ≤2 wt % of the total weight of the composition.

9. The composition as claimed in claim 1, said composition further comprising at least one herb or extract thereof selected from a group consisting of *Piper longum, Solanum xanthocarpum, Tinospora cordifolia, Trichosanthes dioica, Holarrhena antidysenterica, Cyperus rotundus, Swertia chirata, Picrorhiza kurroa, Zingiber officinale, Piper nigrum, Alpinia galanga, Glycyrrhiza glabra, Acorus calamus* and *Oldenlandia corymbosa*.

10. The composition as claimed in claim 1, said composition further comprising at least one herb or extract thereof selected from a group consisting of *Piper longum* in an amount of ≤2 wt % of the total weight of the composition, *Solanum xanthocarpum* in an amount of ≤2 wt % of the total weight of the composition, *Tinospora cordifolia* in an amount of ≤2 wt % of the total weight of the composition, *Trichosanthes dioica* in an amount of ≤2 wt % of the total weight of the composition, *Holarrhena antidysenterica* in an amount of ≤2 wt % of the total weight of the composition, *Cyperus rotundus* in an amount of ≤2 wt % of the total weight of the composition, *Swertia chirata* in an amount of ≤2 wt % of the total weight of the composition, *Picrorhiza kurroa* in an amount of ≤2 wt % of the total weight of the composition, *Zingiber officinale* in an amount of ≤2 wt % of the total weight of the composition, *Piper nigrum* in an amount of ≤2 wt % of the total weight of the composition, *Alpinia galanga* in an amount of ≤2 wt % of the total weight of the composition, *Glycyrrhiza glabra* in an amount of ≤2 wt % of the total weight of the composition, *Acorus calamus* in an amount of ≤2 wt % of the total weight of the composition, and *Oldenlandia corymbosa* in an amount of ≤2 wt % of the total weight of the composition.

11. The composition as claimed in claim 1, further comprising a suitable excipient.

12. The composition as claimed in claim 11, wherein said suitable excipient is gum acacia present in an amount in the range of 8 to 12 wt % of the total weight of the composition.

13. The composition as claimed in claim 1, comprising *Emblica officinalis* in an amount ranging from 6 to 10 wt % of the total weight of the composition, *Terminalia chebula* in an amount ranging from 6 to 10 wt % of the total weight of the composition, *Terminalia bellerica* in an amount ranging from 6 to 10 wt % of the total weight of the composition, *Commiphora mukul* in an amount ranging from 6 to 10 wt % of the total weight of the composition, *Azadirachta indica* in an amount ranging from 6 to 10 wt % of the total weight of the composition, *Curcuma longa* in an amount ranging from 6 to 10 wt % of the total weight of the composition, *Piper longum* in an amount of ≤2 wt % of the total weight of the composition, *Solanum xanthocarpum* in an amount of ≤2 wt % of the total weight of the composition, *Tinospora cordifolia* in an amount of ≤2 wt % of the total weight of the composition, *Trichosanthes dioica* in an amount of ≤2 wt % of the total weight of the composition, *Holarrhena antidysenterica* in an amount of ≤2 wt % of the total weight of the composition, *Cyperus rotundus* in an amount of ≤2 wt % of the total weight of the composition, *Swertia chirata* in an amount of ≤2 wt % of the total weight of the composition, *Picrorhiza kurroakurroa* in an amount of ≤2 wt % of the total weight of the composition, *Zingiber officinale* in an amount of ≤2 wt % of the total weight of the composition, *Piper nigrum* in an amount of ≤2 wt % of the total weight of the composition, *Alpinia galanga* in an amount of ≤2 wt % of the total weight of the composition, *Glycyrrhiza glabra* in an amount of ≤2 wt % of the total weight of the composition, *Acorus calamus* in an amount of ≤2 wt % of the total weight of the composition, *Oldenlandia corymbosa* in an amount of ≤2 wt % of the total weight of the composition, *Tankana Bhasma* in an amount of ≤2 wt % of the total weight of the composition, Swarna makshika Bhasma in an amount of ≤2 wt % of the total weight of the composition, *Mukta Shukti* Bhasma in an amount of ≤2 wt % of the total weight of the composition, Shuddha gairika in an amount of ≤2 wt % of the total weight of the composition, Kapardika bhasma in an amount of ≤2 wt % of the total weight of the composition, Gandhaka in an amount ranging from 6 to 10 wt % of the total weight of the composition; and gum acacia in an amount ranging from 8 to 12 wt % of the total weight of the composition.

14. The composition as claimed in claim 13, wherein said composition is in the form of tablet.

15. The composition as claimed in claim 14, wherein said tablet is in the form of 500 mg tablet.

16. A process for the preparation of composition claimed in claim 1, comprising:
   levigating at least one ingredient selected from a group consisting of Bhasma, Shuddha gairika and Gandhaka in a grinder for a period of 3 hours;
   adding finely powdered herbs comprising dry fruits of *Emblica officinalis*, *Terminalia chebula* and *Terminalia bellerica*; dry stem bark of *Azadirachta indica*; and dry rhizome of *Curcuma longa* to said grinder and grinding while adding grinding decoction comprising *Asparagus racemosus*, wherein said grinding decoction is prepared by soaking one part of fresh roots of *Asparagus racemosus* in 16 parts of water and boiling at a temperature in the range of 80° C. to 85° C. for a period until ⅛$^{th}$ of liquid remains;
   adding at least one herb juice selected from a group consisting of *Dhattura Rasa, Bhringaraja Rasa, Tulasi Rasa* and *Ardraka Rasa* to said grinder while continuing grinding to obtain a ground mass; and
   adding oleo-gum resin of *Commiphora mukul* to said ground mass and grinding for a period of 1 to 3 hours.

17. The process as claimed in claim 16, wherein said bhasma is at least one bhasma selected from a group consisting of *Tankana Bhasma*, Swarna makshika Bhasma, Muktha Sukthi Bhasma and Kapardika bhasma.

18. The process as claimed in claim 16, wherein said grinding is performed for a period of 72 hours.

19. The process as claimed in claim 16, wherein said finely powdered herbs further comprises dry powder of fruits of *Piper longum*, fruits of *Piper nigrum*, stem bark of *Holarrhena antidysenterica*, rhizome of *Acorus calamus*, rhizome of *Zingiber officinale*, whole plant of *Solanum xanthocarpum*, whole plant of *Oldenlandia corymbosa*, whole plant of *Trichosanthes dioica*, whole plant of *Swertia chirata*, stem of *Tinospora cordifolia*, tuber of *Cyperus rotundus*, roots of *Picrorhiza kurroakurroa*, roots of *Alpinia galanga*, and roots of *Glycyrrhiza glabra*.

20. The process as claimed in claim 16, wherein said grinding decoction further comprises *Emblica officinalis, Terminalia chebula, Terminalia bellerica, Aloe vera, Swertia chirata, Stereospermum suaveolens, Premna mucronate, Gmelina arborea, Aegle marmelos, Oroxylum indicum, Desmodium gangeticum, Uraria pitta, Solanum indicum, Solanum xanthocarpum, Tribulus terrestris, Adhatoda vasica, Phyllanthus niruri, Ocimum sanctum, Ricinus communis* and *Plumbago rosea*.

21. The process as claimed in claim 16, wherein said process further comprises adding gum acacia and grinding to obtain a semisolid mass; and drying said semi solid mass at a temperature in the range of 40 to 60 degree Celsius.

22. The process as claimed in claim 21, wherein said grinding is performed for a period of 1 to 3 hours.

* * * * *